United States Patent
Arndt et al.

(10) Patent No.: US 8,008,932 B2
(45) Date of Patent: Aug. 30, 2011

(54) COMPONENT WITH A DETECTION STRUCTURE FOR MECHANICAL DAMAGE

(75) Inventors: Frank Arndt, Berlin (DE); Ursus Krüger, Berlin (DE); Oliver Stier, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 257 days.

(21) Appl. No.: 12/310,855

(22) PCT Filed: Sep. 10, 2007

(86) PCT No.: PCT/EP2007/059464
§ 371 (c)(1),
(2), (4) Date: Mar. 10, 2009

(87) PCT Pub. No.: WO2008/031792
PCT Pub. Date: Mar. 20, 2008

(65) Prior Publication Data
US 2009/0315573 A1    Dec. 24, 2009

(30) Foreign Application Priority Data
Sep. 13, 2006 (DE) .......................... 10 2006 043 781

(51) Int. Cl.
*G01R 27/08* (2006.01)
*G01N 27/00* (2006.01)
(52) U.S. Cl. ....................... 324/693; 324/557
(58) Field of Classification Search .................. 324/693, 324/557
See application file for complete search history.

(56) References Cited

U.S. PATENT DOCUMENTS

| 4,155,758 | A  | 5/1979  | Evans et al.  |
| 4,484,132 | A  | 11/1984 | Crites        |
| 6,123,874 | A  | 9/2000  | Fukaya et al. |
| 7,141,990 | B2 | 11/2006 | Bast et al.   |
| 2005/0212535 | A1 | 9/2005 | Bast et al.  |
| 2006/0132149 | A1 | 6/2006 | Twerdochlib  |

FOREIGN PATENT DOCUMENTS

| DE | 19810674 A1    | 10/1998 |
| DE | 19923143 A1    | 11/2000 |
| DE | 10223985 A1    | 12/2003 |
| DE | 102004030295 B3 | 11/2005 |
| DE | 102004047699 A1 | 4/2006  |
| DE | 102005028250 A1 | 12/2006 |
| EP | 0300380 B1     | 1/1989  |
| WO | WO 2006000520 A1 | 1/2006 |
| WO | WO 2006034907 A1 | 4/2006 |

*Primary Examiner* — Vincent Q Nguyen

(57) ABSTRACT

A component made of electrically insulating material with a detection structure for mechanical damage such as cracks is disclosed. The detection structure is a conductor. The electrical properties of the detection structure are modified as more and more cracks are formed such that the component will be replaced in time before breaking. The electrical conductor is formed by particles that are in contact with each other and have a metallic surface such that an electrical conductor is created which is particularly sensitive to mechanical damage, thus rendering the detection structure highly sensitive. Furthermore, if the metallic surface is produced merely by cladding the particles while the inside of the particles is made of the same material as the component, a conductor featuring an adapted thermal expansion behavior is created for components that are subject to great thermal stress, e.g. heat shield panels.

18 Claims, 2 Drawing Sheets

COMPONENT WITH A DETECTION STRUCTURE FOR MECHANICAL DAMAGE

CROSS REFERENCE TO RELATED APPLICATIONS

This application is the US National Stage of International Application No. PCT/EP2007/059464 filed Sep. 10, 2007 and claims the benefit thereof. The International Application claims the benefits of German Patent application No. 10 2006 043 781.0 DE filed Sep. 13, 2006, both of the applications are incorporated by reference herein in their entirety.

FIELD OF INVENTION

The invention relates to a component of an electrically insulating material incorporating a structure for detecting mechanical damage to the component, the detection structure having an electrical conductor which is fixedly connected to the component and whose geometry is matched to the geometry of the component such that mechanical damage to the component is associated with a change in the electrical properties of the electrical conductor.

BACKGROUND OF INVENTION

A component of the type mentioned in the introduction is described, for example, in DE 102 23 985 A1. The component is a heat shield panel which is preferably made of ceramic. Due to constant thermal loading of the heat shield panel which may be installed, for example, in a gas turbine combustion chamber, there is a risk of it being mechanically damaged by aging processes. The mechanical damage normally consists in the formation of cracks in the brittle material which grow progressively over its service life. Once crack growth has reached a particular stage, the reliability of the heat shield panel is reduced in a no longer acceptable manner, as it could come loose from its anchorage, for example. In order to be able to identify this point in time, a structure for detecting mechanical damage is provided. Adapting the geometry of said detection structure to the component's geometry ensures that, in the event of crack formation, the detection structure implemented by an electrical conductor is damaged in such a way that its electrical properties change, particularly its electrical conductivity. This change can be used to characterize impermissibly far advanced crack formation, analysis of electrical signals of the detection structure enabling a decision to be made as to when a heat shield panel must be replaced.

A fixed connection between the electrical conductor and the component can be established on the surface of the component either, for example, by placing a ceramic conductor onto the surface, or placing it in grooves running on the surface and burning it together with the ceramic component. Another possibility is to provide the electrical conductor inside the component. For example, an electrically conductive material can be accommodated in the form of a loop inside a heat shield panel by inserting the loop in the green body during the production thereof.

EP 300 380 A1 discloses that mica particles can be provided with an electrically conductive coating of silver and used in an organopolysiloxane compound. This produces a heat-curable composite material which develops electrically conductive properties after curing. Because of mica's crystal structure, the mica particles are particles that have strongly anisotropic mechanical properties.

SUMMARY OF INVENTION

An object of the invention is to specify a component having an electrical conductor as a damage detection structure in which the electrical conductor reacts comparatively sensitively to damage.

This object is achieved according to the invention by the component described in the introduction, wherein the electrical conductor is constituted by mutually contacting particles with a metallic surface, by the measures which will now be explained in greater detail, using particles with a metallic shell and a core matched to the component properties.

The electrical conductor is therefore rendered conducting by the particles with the metallic surface being in contact with one another so that an exchange of electrons can take place between the particles having the metallic surface, thereby intentionally producing particularly sensitive areas of the electrical conductor at the contact surfaces of the particles, resulting in a significant change in the electrical properties of the electrical conductor in the event of damage to the component (particularly crack growth intersecting the electrical conductor). In particular, the resistivity of the electrical conductor is relatively greatly changed.

Because of the manufacturing process, production of the electrical conductor from the particles with a metallic surface may result in melting of the metal constituting the metallic surface, so that the association of particles forming the electrical conductor is consolidated. However, at the transitions between the now intimately connected particles, the sensitivity of the resulting electrical conductor to mechanical stresses remains high. It is also possible that the metallic surfaces of the particles are not melted during component production. This is the case if the melting point of the metal used is above the temperatures occurring during manufacture of the component. For plastic components, this will be the case for the majority of the metals. For ceramic components which must undergo tempering for their production, suitable high-melting metals such as tungsten can be used.

It is provided that the particles consist of an electrically insulating core with a metallic shell. This means that, even if the metal melts, a structure of the resulting electrical conductor is produced which is not solidly constituted but, but in addition to the pores formed between the particles, also has sub-regions which are filled by the electrically insulating core material of the particles. The resulting sponge-like structure of the conductor also advantageously develops a particular sensitivity to mechanical damage.

In addition, it is provided that the core consists of a material that is matched to the material of the component in respect of its mechanical behavior, in particular of its thermal expansion behavior. Particularly in the case of thermally stressed components such as heat shield panels, the advantage of this is that electrical conductors placed inside the component exhibit a thermal expansion behavior matched to the thermal expansion behavior of the surrounding component. This enables stresses that would occur due to differential thermal expansion of two different materials, and could result in mechanical overloading of the component, to be avoided. In general, metallic materials have, for example, a higher coefficient of thermal expansion than ceramic components, which makes it more difficult to use metallic conductors in ceramic heat shield panels. For example, in addition to stressing a component, differential thermal expansion of component and electrical conductor also causes the measurement result to be obtained by means of the electrical conductor to be falsified if the latter is deformed by the stresses occurring. Therefore, by matching the thermal expansion behavior of electrical conductor and component, the sensitivity of the measurement method can also be improved to the extent that the possibility of measurement errors occurring is reduced. It is particularly advantageous to select an identical material for core and shell, as this ensures optimum matching of the mechanical properties of the electrical conductor and the surrounding component.

The above comments obviously also apply to electrical conductors mounted on the surface of the component. Here, different coefficients of thermal expansion may even result in peeling of the electrical conductor from the surface, which would completely destroy the structure for detecting mechanical damage. This could give rise, for example, to incorrect information which would be interpreted as meaning that damage to the component, in particular progressive crack growth, has reached a stage where replacement of the component is necessary.

According to a particular embodiment of the invention it is provided that the particles with the metallic surface in the electrical conductor are present mixed with particles totally consisting of an electrically insulating material, in particular the material of the component. This advantageously ensures that the filling degree of metal in the electrical conductor is further reduced. In addition to the pores between the particles or rather any non-metallic cores of the particles, sub-regions are then also present in the electrical conductor which are constituted by the particles consisting wholly of an electrically insulating material. Due to the reduction of the filling degree of metallic material in the electrical conductor, the latter is, according to the mechanism already described, advantageously even more sensitive to mechanical damage, thereby further increasing the sensitivity of the detection structure.

As already explained, using the detection structure is particularly advantageous if the mechanical damage to be detected is crack formation in the component, the conductor in this case running such that it is intersected by the likely crack growth. This advantageously ensures that the crack growth, when it has arrived at the surface of the conductor, preferably begins to split the conductor at right angles to its path, thereby producing the greatest possible change in the electrical properties of the conductor in relation to the progressive crack growth. This makes it possible to achieve a change in the electrical properties as soon as the crack has arrived at the conductor used as a detection structure and then progresses further.

It is particularly advantageous if the conductor runs parallel to the surface of the component. This takes account of the situation whereby cracks usually propagate in the components from the surface to the inside of the component, thereby resulting in progressive mechanical weakening of the relevant component cross-section. Crack growth ends in mechanical failure of the component, the detection structure being designed to prevent component failure. If the conductors are placed parallel to the surface of the component, it should also be noted that conductor breakage due to crack growth takes place before the crack results in component failure.

It is particularly advantageous if a plurality of mutually independent conductors is provided which run at different spacings parallel to the surface. This not only ensures timely replacement of the component prior to failure of same, but also enables information about the condition of the component to be obtained at an earlier stage of crack propagation. If mutually independent conductors are present, progressive crack growth will reach adjacent independent conductors one after the other with increasing distance of the crack propagation front from the surface, thereby enabling the present course of the crack propagation front to be assessed.

The electrical conductors can be evaluated in respect of the property to be monitored, e.g. the electrical resistance, by means of electrical contacting. In this case, for example, a direct or alternating current can be passed through the electrical conductor, enabling the resistance to be determined. Another possibility for determining the properties of the electrical conductor is contactless. Here, electromagnetic excitation in the RF range is produced which elicits a response from the conductor in question. This can be detected contactlessly e.g. by means of an antenna. For this embodiment of the detection structure it is advantageous if the path of independent conductors is implemented such that they produce mutually different spectral signatures in response to the high-frequency electromagnetic excitation. The spectral signature of one of the conductors is taken to mean a mathematical function whereby the response of the electrical conductor in respect of the electrical property considered is determined as a function of a frequency spectrum of the excitation. In order to be able to generate different spectral signatures in this excitation range, it is necessary to vary the electrical properties of the different mutually independent conductors. This can be achieved, for example, by the layout of the conductors in the component, by the thickness of the conductors and by the choice of conductor material, the arrangement of the particles in the manner already described also possibly contributing to the variation in the electrical properties. If the mutually independent conductors are differentiable in respect of their spectral signature, it becomes advantageously possible to ascertain the changes in the electrical properties of a particular conductor, as a change in their spectral signature can be unequivocally related to it. On the other hand, a conductor's mechanical damage, in particular its splitting due to crack formation in the component, must not make that conductor's spectral signature so unrecognizable that the changed signature of the conductor no longer has sufficient differentiability from the signatures of the other conductors. In this case the local information would be lost.

According to a particular embodiment of the invention it is provided that the conductor runs in a loop. This can be advantageously placed along the edge of a component of flat design such as a heat shield panel, for example. Moreover, using looped conductors enables particularly characteristic signatures for high-frequency excitation to be produced which also change in an easily verifiable manner due to breakage of the loop in a particular crack growth scenario.

BRIEF DESCRIPTION OF THE DRAWINGS

Further details of the invention will now be described with reference to the accompanying drawings. Identical or corresponding elements are provided with the same reference characters in the respective Figures and only re-explained where differences arise between the individual Figures.

DETAILED DESCRIPTION OF INVENTION

Figure 1:
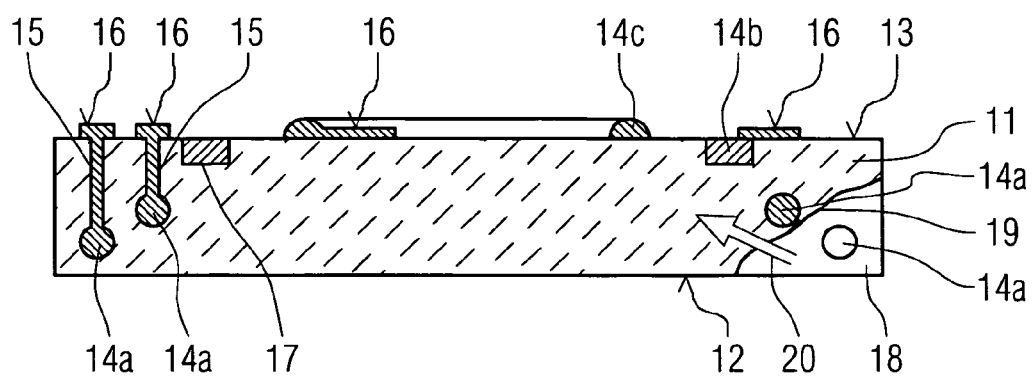
FIG. 1 shows a cross-sectional view of a heat shield panel as an exemplary embodiment of the component according to the invention.

A component 11, as shown in FIG. 1, is implemented as a heat shield panel e.g. for a gas turbine combustion chamber. This component has a front side 12 facing into the combustion chamber, this side being most heavily subjected to the thermal stress produced by the combustion process, and a back side 13 by which it can be fixed to the wall (not shown in greater detail) of the combustion chamber. The component 11 is made of ceramic. Placed inside the component are electrical conductors 14a which can run in a loop (not visible in the illustration in FIG. 1). These conductors 14a have electrical connections 15 to the back side 13 of the component 11 which are electrically contactable via contact surfaces 16. Accommodated in a groove 17 is another conductor 14b which likewise forms a loop (not shown in greater detail) on the back side 13. There is also implemented on the component surface formed by the back side 13 a raised conductor 14c which likewise runs in a loop. The conductors 14b and 14c also have contact surfaces 16 for their contacting. As the contact surfaces are disposed on the back side 13 of the component 11 and the thermal stress to which the contact surfaces 16 are subjected can be kept within limits, contacting of the installed heat shield panel is possible even during operation.

The cross section shown in FIG. 1 also runs precisely through a crack 18 propagating with a crack front 19 in the direction of the arrow 20 in the component 11. In this process, the outermost of the conductors 14a has already been cut through so that a circuit can no longer be completed when said conductor is electrically contacted. As the conductors 14a, 14b, 14c all run parallel to the surface constituted by the front side 12 of the component, the failure of the first conductor 14a is indirectly indicative of the advance of the crack. Further crack growth will cause the other conductor 14a, the conductor 14b and finally the conductor 14c also to be successively cut through.

Figure 2:
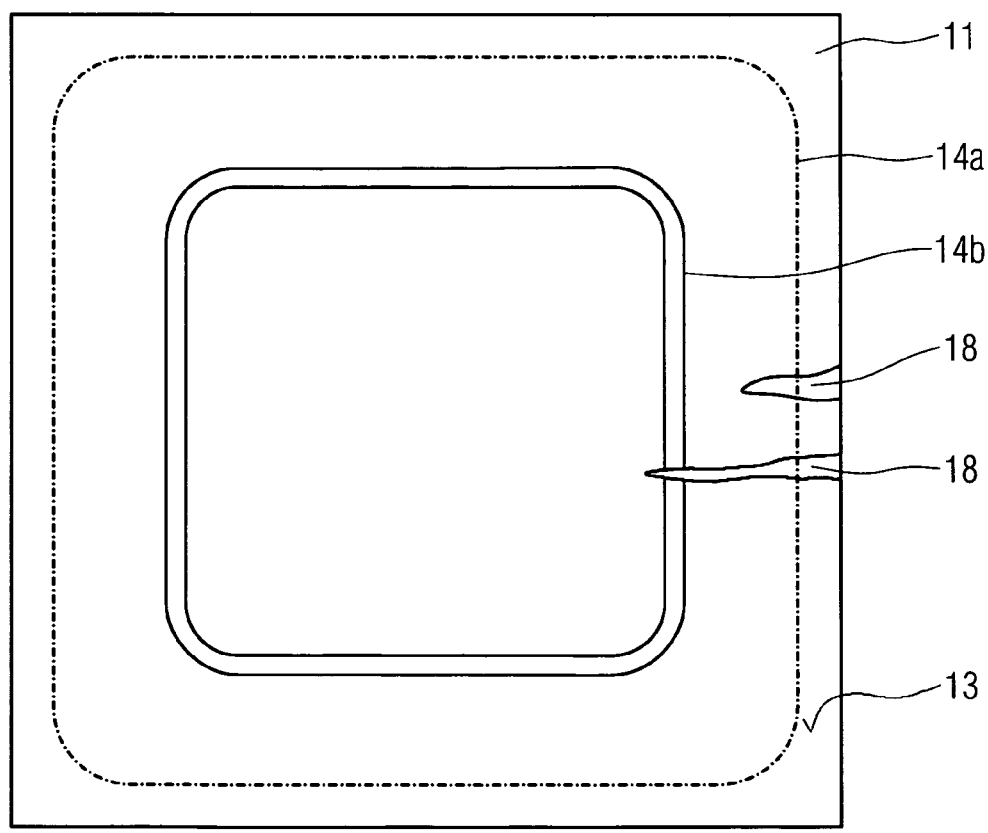
FIG. 2 shows a plan view of a heat shield panel as another exemplary embodiment of the component according to the invention.

FIG. 2 shows a possible looped arrangement of the conductors 14a, 14b with a constant distance from the edge of the plate-shaped component 11. It can also be seen how progressive growth of the cracks 18 successively cuts first the outer loop 14a and then the inner loop 14b. Unlike in FIG. 1, the conductors 14a, 14b as shown in FIG. 2 are implemented as induction loops, i.e. they have no contact surfaces 16 and are of closed design.

As shown in FIGS. 3 to 6, the electrical conductors 14 can consist of metallic particles 21 or of particles 22 comprising a non-metallic core 23 and a metallic shell 24. In addition, further particles 25 of an electrically insulating material can be provided in the conductors 14. The component 11, which is shown only as a sub-region bordering the electrical conductor 14, is fixedly connected to the conductor 14, it being possible for the segment showing the respective transition between component 11 and conductor 14 according to FIGS. 3 to 6 to represent all the possible arrangements of the conductors 14a, 14b or 14c on the component.

Different structures of the conductors consisting of particles 21, 22, 25 will now be explained in greater detail, further combinations of the variants explained in the Figures being obvious to the average person skilled in the art. The particles 21, 22, 25 used can be implemented as microparticles (i.e. with dimensions of approx. 0.1 to 500 μm) or as nanoparticles (i.e. with dimensions of no more than 100 nm).

Figure 3:
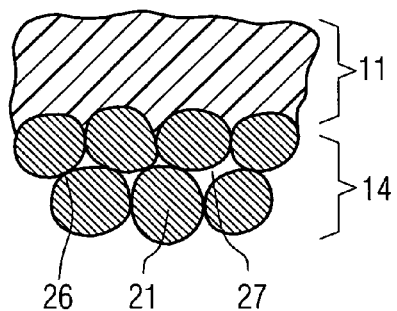
FIGS. 3 and 4 show electrical conductors according to the prior art.

The electrical conductor 14 according to FIG. 3 is constituted by metallic particles 21. This means that the particles 21 consist of solid metal. Adjacent particles 21 are in contact with one another at contact points 26, voids 27 between the particles reducing the effective cross section of the electrical conductor 14 and thus increasing the sensitivity to damage caused to the conductor 14 e.g. by progressive crack growth in the component 11.

The component 11 consists, for example, of plastic, with the particles 21 being molded therein. In the associated manufacturing process, temperatures are produced which are insufficient to melt the particles 21. The points of contact of the adjacent particles are therefore retained without material fusion between the adjacent particles 21.

Figure 4:
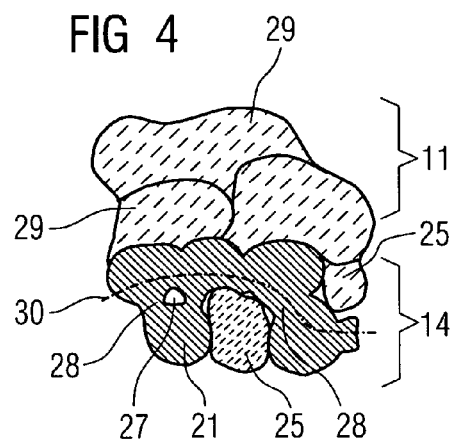

The component 11 according to FIG. 4 consists of a ceramic and could constitute, for example, a heat shield panel. Metallic particles 21 are again used as the electrical conductor 14, these having been melted at least on their surface as a result of the heat treatment associated with the manufacture of the component 11 and therefore having formed a bond 28 to one another, but with voids 27 between the fused particles 21 nevertheless remaining.

In addition, as well as the metallic particles 21, other particles 25 of the same ceramic material as the component 11 have been used to implement the structure of the electrical conductor 14. These can be, for example, enclosed by the metallic particles 21 or even bonded to the material of the component 11 at the boundary with the component 11 by the heat treatment carried out. Also indicated are the edges of ceramic particles 29 which constitute the microstructure of the component 11.

FIG. 4 also shows that the other particles 25 must only be added to the metallic particles 21 in the material of the conductor 14 in such a concentration that the metallic particles 21 reliably form a cohesive structure. Only in this way can electrical conduction paths 30, indicated as a dash-dotted line in the electrical conductor 14, be formed which ensure the electrical conductivity of the conductor 14.

Figure 5:
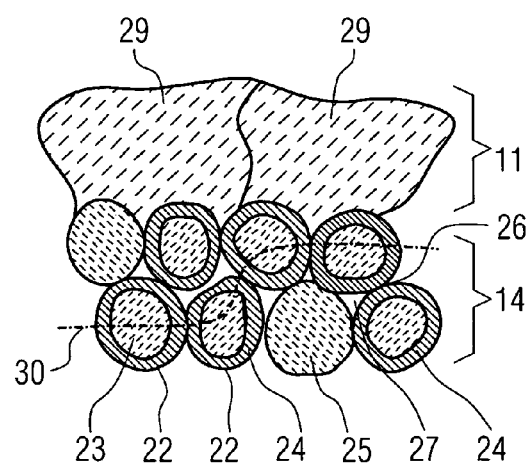
FIGS. 5 and 6 show segments of different examples of electrical conductors that can be used in the component according to the invention.

In the case of the electrical conductor 14 according to FIG. 5, particles 22 each consisting of a metallic shell 24 and an electrically insulating core 23 are used to conduct the electric current. In addition, other particles 25 can be provided which consist of the material of the component 1. The cores 23 of the particles 22 can also consist of this material. In contrast to FIG. 4, the metallic material of the shell 24 is sufficiently temperature-resistant not to be melted by the heat treatment forming the component 11. As described with reference to FIG. 3, the particles 22 are therefore present in the unmelted state so that only contact points 26 are created to constitute the conduction paths 30.

The advantage of using the material of the component 11 for the other particles 25 and the cores 23 is that the conductor 14 exhibits a behavior closely matched to the thermal expansion behavior of the component 11 when the component 11 is subjected to thermal loading. The stresses occurring in the electrical conductor 14 due to the thermal expansions occurring when the component 11 is heated are therefore minimized, so that a change in the electrical properties of the conductor 14 because of mechanical loading of same only occurs when the component 11 is damaged e.g. due to crack formation. Thermal loading alone changes the electrical properties of the conductor 14 only in a reversible and temperature-dependent manner and is therefore predictable by means of a temperature measurement and must be taken into account.

Figure 6:
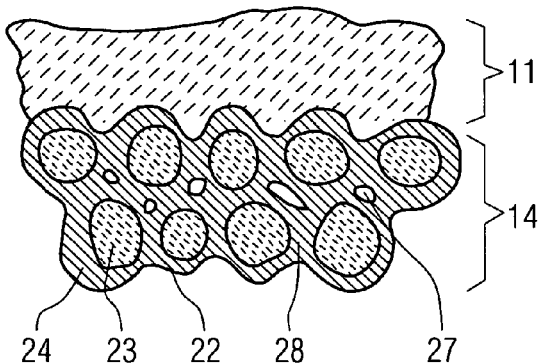

The electrical conductor 14 according to FIG. 6 likewise consists of particles 22 with a core 23 and a shell 24. The shells 24 of the particles 22 were melted during manufacture of the component 11, so that with simultaneous formation of voids 27, a fused connection 28 of the metallic material for forming the electrical conductor has been produced. The effective cross section of the conductor 14 is in this case mainly reduced by the cores 23, but also by the voids 27.

The cores 23 are not made of the same material as the component 11. However, the material of the cores 23 is matched to the component 11 in respect of thermal expansion behavior. This makes it possible to achieve the temperature insensitivity, explained with reference to FIG. 5, of the electrical conductor having regard to an unwanted change in its electrical properties because of mechanical overstressing.

The invention claimed is:

1. A component of an electrically insulating material comprising:
    a geometry;
    a detection structure for detecting mechanical damage to the component;
    an electrical conductor which is part of the detection structure and fixedly connected to the component, the electrical conductor being constituted by mutually contacting particles having a metallic surface, the particles consisting of an electrically insulating core with a metallic shell;
    wherein the detection structure has a geometry which matches to the geometry of the component such that mechanical damage to the component is associated with a change in electrical properties of the electrical conductor, and
    wherein the core consists of a material which in terms of its thermal expansion behavior is matched to a thermal expansion behavior of the material of the component.

2. The component as claimed in claim 1, wherein the material of the core is identical to the material of the component.

3. The component as claimed in claim 2, wherein the particles having the metallic surface of the electrical conductor are mixed with particles wholly consisting of an thermally insulating material.

4. The component as claimed in claim 3, wherein the thermally insulating material is the material of the component.

5. The component as claimed in claim 1, wherein the particles having the metallic surface of the electrical conductor are mixed with particles wholly consisting of a thermally insulating material.

6. The component as claimed in claim 5, wherein the thermally insulating material is the material of the component.

7. The component as claimed in claim 5, wherein the mechanical damage to be detected is crack formation in the component, the conductor running such that it is intersected by the likely crack growth.

8. The component as claimed in claim 7, wherein the conductor runs parallel to a surface of the component.

9. The component as claimed in claim 8, further comprising a plurality of mutually independent conductors are provided running at different spacings parallel to the surface.

10. The component as claimed in claim 9, wherein the independent conductors run such that they produce different spectral signatures in response to high-frequency electromagnetic excitation.

11. The component as claimed in claim 1, wherein the mechanical damage to be detected is crack formation in the component, the conductor running such that it is intersected by the likely crack growth.

12. The component as claimed in claim 11, wherein the conductor runs parallel to a surface of the component.

13. The component as claimed in claim 12, further comprising a plurality of mutually independent conductors are provided running at different spacings parallel to the surface.

14. The component as claimed in claim 13, wherein the independent conductors run such that they produce different spectral signatures in response to high-frequency electromagnetic excitation.

15. The component as claimed in claim 1, wherein the conductor runs in a loop.

16. The component as claimed in claim 1, wherein the component is implemented as cladding for heat shielding purposes.

17. The component as claimed in claim 1, wherein the component is a heat shield panel made of ceramic.

18. The component as claimed in claim 17, wherein the heat shield panel is installed in a gas turbine combustion chamber.

* * * * *